United States Patent [19]

Li et al.

[11] Patent Number: 5,653,922

[45] Date of Patent: *Aug. 5, 1997

[54] POLYMERIC MICROBEADS AND METHOD OF PREPARATION

[75] Inventors: Nai-Hong Li, Edmonton, Canada; James R. Benson, Los Gatos; Naotaka Kitagawa, Fremont, both of Calif.

[73] Assignee: Biopore Corporation, Los Gatos, Calif.

[*] Notice: The portion of the term of this patent subsequent to Jun. 6, 2014, has been disclaimed.

[21] Appl. No.: 485,494

[22] Filed: Jun. 7, 1995

Related U.S. Application Data

[63] Continuation-in-part of Ser. No. 254,303, Jun. 6, 1994, Pat. No. 5,583,162.
[51] Int. Cl.$^6$ .............................. B01J 13/02; B01J 13/20; B01J 13/22
[52] U.S. Cl. ........................... 264/4.3; 264/4.33; 264/4.7
[58] Field of Search ................................ 264/4.3, 4.33, 264/4.7

[56] References Cited

U.S. PATENT DOCUMENTS

| | | | |
|---|---|---|---|
| 3,255,127 | 6/1966 | von Bonin et al. | |
| 3,822,224 | 7/1974 | Gillan et al. | |
| 3,879,314 | 4/1975 | Gunning et al. | |
| 3,891,577 | 6/1975 | Kershaw et al. | |
| 3,923,704 | 12/1975 | Gunning et al. | |
| 3,933,579 | 1/1976 | Kershaw et al. | 162/164 |
| 3,988,508 | 10/1976 | Lissant | 526/344 |
| 4,137,380 | 1/1979 | Gunning et al. | 521/62 |
| 4,321,332 | 3/1982 | Beresford et al. | 523/502 |
| 4,522,953 | 6/1985 | Barby et al. | |
| 4,536,521 | 8/1985 | Haq. | |
| 4,611,014 | 9/1986 | Jomes et al. | |
| 4,612,334 | 9/1986 | Jones et al. | |
| 4,629,742 | 12/1986 | Brady et al. | 521/55 |
| 4,742,086 | 5/1988 | Masamizu et al. | 521/62 |
| 4,755,655 | 7/1988 | Edwards et al. | |
| 4,788,255 | 11/1988 | Edwards et al. | |
| 4,965,289 | 10/1990 | Sherrington et al. | |
| 4,985,468 | 1/1991 | Elmes et al. | |
| 5,147,345 | 9/1992 | Young et al. | |
| 5,149,720 | 9/1992 | DesMarais et al. | |
| 5,189,070 | 2/1993 | Brownscombe et al. | 521/64 |
| 5,200,433 | 4/1993 | Beshouri | 521/63 |
| 5,252,619 | 10/1993 | Brownscombe et al. | |
| 5,268,097 | 12/1993 | Girot et al. | |
| 5,306,733 | 4/1994 | Adamski et al. | 521/63 |
| 5,306,734 | 4/1994 | Bass et al. | 521/63 |
| 5,318,554 | 6/1994 | Young et al. | 604/378 |
| 5,331,015 | 7/1994 | DesMarais et al. | 521/62 |

FOREIGN PATENT DOCUMENTS

| | | |
|---|---|---|
| 0 060 138 | 9/1982 | European Pat. Off. . |
| 0 105 634 | 4/1984 | European Pat. Off. . |
| 0 239 360 | 9/1987 | European Pat. Off. . |
| 0 288 310 | 10/1988 | European Pat. Off. . |
| 0 289 238 | 11/1988 | European Pat. Off. . |
| 0 467 528 A2 | 1/1992 | European Pat. Off. . |
| 193901 | 11/1984 | Japan . |
| 1288583 | 9/1972 | United Kingdom . |
| 1332469 | 10/1973 | United Kingdom . |
| WO81/01711 | 6/1981 | WIPO . |
| WO84/00764 | 3/1984 | WIPO . |
| WO95/31485 | 11/1995 | WIPO . |

OTHER PUBLICATIONS

Tijssen, P., "Nature of Protein–Plastic Interaction," *Practice & Theory of Enzyme Immunoassays* 298–314 (Elsevier 1985).

Williams, J., "Toroidal Microstructures from Water–in–Oil Emulsions," 4 *Langmuir* 44–49 (1988).

Williams, J. and Wrobleski, D., "Spatial Distribution of the Phases in Water–in–Oil Emulsions. Open and Closed Microcellular Foams from Cross–Linked Polystyrene," 4 *Langmuir* 656–662 (1987).

Arshady, R., "Suspension, Emulsion, and Dispersion Polymerization: A Methodological Survey," 270 *Colloid & Polymer Science* 717–732 (1992).

Even, W. and Gregory, D., "Emulsion–Derived Foams: Preparation, Properties, and Application," *MRS Bulletin* 29–33 (Apr. 1994).

Hainey, P. et al., "Synthesis and Ultrastructural Studies of Styrene–Divinylbenzene Polyhipe Polymers," 24 *Macromolecules* 117–121 (1991).

Lee, D., et al., "High Density BHK Culture Using Porous Microcarriers," *Production of Biologicals from Animal Cell Culture*, Butterworth–Heinemann 480–487 (1992).

Lee, D. et al., "Polystyrene Macroporous Bead Support for Mammalian Cell Culture," 665 *Annals New York Academy of Sciences* 137–145 (1992).

Small, P. and Sherrington, D., "Design and Application of a New Rigid Support for High Efficiency Continuous–flow Peptide Synthesis," 21 *Journal of the Chemical Society* 1589–1591 (1989).

Primary Examiner—Nathan M. Nutter
Attorney, Agent, or Firm—Skjerven, Morrill, MacPherson, Franklin & Friel, LLP; Laura Terlizzi; Emily M. Haliday

[57] ABSTRACT

The present invention relates to porous crosslinked polymeric microbeads having cavities joined by interconnecting pores wherein at least some of the cavities at the interior of each microbead communicate with the surface of the microbead. The present invention also relates to a process for producing a porous, crosslinked polymeric microbead as well as the product of this process. This process involves combining an oil phase with an aqueous discontinuous phase to form an emulsion, adding the emulsion to an aqueous suspension medium to form an oil-in-water suspension of dispersed emulsion droplets, and polymerizing the emulsion droplets to form microbeads. At least 10% of the microbeads produced in accordance with the present invention are substantially spherical or substantially ellipsoidal or a combination of the two.

71 Claims, No Drawings

POLYMERIC MICROBEADS AND METHOD OF PREPARATION

The present application is a continuation-in-part of U.S. Ser. No. 08/254,303, filed Jun. 6, 1994 and now U.S. Pat. No. 5,583,162.

BACKGROUND OF THE INVENTION

1. Field of the Invention The present invention relates to microbeads of a crosslinked porous polymeric material and methods for preparing such microbeads. In particular, this invention is directed to a polymeric microbead of exceptionally high porosity.

2. Description of the Prior Art

Crosslinked, homogeneous, porous polymeric materials are disclosed in U.S. Pat. No. 4,522,953 (Barby et al., issued Jun. 11, 1985). The disclosed polymeric materials are produced by polymerization of water-in-oil emulsions having a relatively high ratio of water to oil. These emulsions are termed "high internal phase emulsions" and are known in the art as "HIPEs". HIPEs comprise an oil continuous phase including a monomer and a crosslinking agent and an aqueous discontinuous phase. Such emulsions are prepared by subjecting the combined oil and water phases to agitation in the presence of an emulsifier. Polymers are produced from the resultant emulsion by heating. The polymers are then washed to remove any unpolymerized monomer/crosslinker.

The disclosed porous polymers have rigid structures containing cavities interconnected by pores in the cavity walls. By choosing appropriate component and process conditions, HIPE polymers with void volumes of 80% or more can be achieved. These materials thus have a very high capacity for absorbing and retaining liquids.

Various modifications of HIPE polymers have been described. For instance, U.S. Pat. No. 4,536,521 (Haq, issued Aug. 20, 1985) discloses that HIPE polymers can be sulfonated to produce a sulfonated polymeric material that exhibits a high capacity for absorption of ionic solutions. Other functionalized HIPE polymers prepared by a similar process have been disclosed in U.S. Pat. Nos. 4,611,014 (Jomes et al., issued Sep. 9, 1986) and 4,612,334 (Jones et al., Sep. 16, 1986).

Although the existence of polymerizable HIPEs is known, the preparation of useful HIPE polymers is not without its difficulties. Because the emulsions used to produce these polymers have a high ratio of water to oil, the emulsions tend to be unstable. Selection of the appropriate monomer/ crosslinker concentration, emulsifier and emulsifier concentration, temperature, and agitation conditions are all important to forming a stable emulsion. Slight changes in any of these variables can cause the emulsion to "break" or separate into distinct oil and water phases. Furthermore, emulsion components and process conditions that produce a stable emulsion may not always yield HIPE polymers that are useful for their intended purpose.

In addition to these problems, the costs associated with scaling up production of HIPE polymers have prevented commercial development of HIPE polymer-based products. Processes for large-scale production of HIPE polymers are known. For instance, U.S. Pat. No. 5,149,720 (DesMarais et al., issued Sep. 22, 1992) discloses a continuous process for preparing HIPEs that are suitable for polymerization into absorbent polymers. In addition, a method that facilitates such continuous processes by reducing the curing time of monomers in a HIPE is set forth in U.S. Pat. No. 5,252,619 (Brownscombe et al., issued Oct. 12, 1993). Large-scale production of HIPE polymers by such known processes, however, has been hampered by the lack of a cost-efficient means of removing the unpolymerized emulsion components from the polymers.

All prior art processes for making HIPE polymers produce a block of polymeric material the size and shape of the vessel used for polymerization. The problem with producing HIPE polymers in block form is that it is very difficult to wash unpolymerized emulsion components out of a block of low density, highly absorbent material. The attempted solution to this problem has been to grind the blocks into particles, but this approach is unsatisfactory because both the drying and milling processes are costly, and there is a limit to the size of the particles produced by milling. For many applications, the removal of residual emulsion components is essential. Yet, to date, no cost-efficient method for performing this wash step has been developed.

An additional problem with prior art HIPE polymeric blocks is that the blocks have a skin that forms at the interface between the HIPE and the container used for polymerization. (U.S. Pat. No. 4,522,953, Barby et al., issued Jun. 11, 1985, at column 4, lines 1–6). To produce a permeable block, and hence, to produce a useful product, the skin must be removed. Ideally, one would like to be able to produce a polymeric material having the desirable characteristics of HIPE polymers but lacking the skin.

SUMMARY OF THE INVENTION

The present invention includes a material (hereinafter "microbeads") wherein at least about 10% of the material is in the form of substantially spherical and/or substantially ellipsoidal beads. These microbeads have a porous, crosslinked, polymeric structure, characterized by cavities joined by interconnecting pores. At least some of the cavities at the interior of each microbead communicate with the surface of the microbead.

The present invention also includes a process for producing a porous, crosslinked polymeric microbead as well as the product of this process. The first step of this process is to combine an oil continuous phase (hereinafter an "oil phase") with an aqueous discontinuous phase to form an emulsion. The oil phase of the emulsion includes a substantially water-insoluble, monofunctional monomer, a substantially water-insoluble, polyfunctional crosslinking agent, and an emulsifier that is suitable for forming a stable water-in-oil emulsion. The second step of the process is to add the emulsion to an aqueous suspension medium to form an oil-in-water suspension of dispersed emulsion droplets. The final step of this process is polymerizing the emulsion droplets to form microbeads.

In one embodiment, a polymerization initiator is present in both the aqueous discontinuous phase of the HIPE and the aqueous suspension medium. A polymerization initiator can optionally be included in the oil phase as well. In a variation of this embodiment, the oil phase includes styrene as the monomer, divinylbenzene as the crosslinking agent, and sorbitan monooleate as the emulsifier. In addition, the oil phase contains the oil-soluble polymerization initiator azoisobisbutyronitrile as well as dodecane, which promotes the formation of interconnecting pores. The aqueous discontinuous phase includes the water-soluble polymerization initiator potassium persulfate. The aqueous suspension medium includes a suspending agent comprising modified silica and gelatin as well as potassium persulfate. In another embodiment, polymerization initiator is present only in the oil phase.

The present invention also encompasses microbeads that have been modified for use in particular applications. In particular, the present invention includes microbeads functionalized for absorption of liquids; carboniferous structures produced from microbeads and a process for producing such structures; and microbeads having a gel or pre-gel within the microbead cavities as well as a process for producing such microbeads.

In addition, the present invention includes the use of microbeads in a variety of applications including the use of microbeads as a substrate in separation and synthetic methods; the use of microbeads as a substrate for immobilizing a molecule such as a polypeptide or an oligonucleotide; and the use of microbeads in cell culture methods.

DETAILED DESCRIPTION OF THE INVENTION

The Microbeads

The present invention includes a crosslinked porous polymeric material, termed "microbeads", wherein at least about 10% of the microbeads are substantially spherical and or substantially ellipsoidal. The present invention also includes a process for making such a material. A microbead is typically produced by suspension polymerization of a high internal phase emulsion, termed a "HIPE". The microbead of the present invention thus has many of the desirable physical characteristics of prior art HIPE polymers (such as those disclosed in U.S. Pat. No. 4,522,953, Barby et al., issued Jun. 11, 1985, which is incorporated by reference herein in its entirety). Specifically, the microbead has a very low density due to the presence of cavities joined by interconnecting pores. The bulk density of a batch of microbeads in accordance with the present invention is typically less than about 0.2 gm/ml. The void volume of the microbead is high, preferably at least about 70% and, more preferably at least about 90%. This high porosity gives the microbead exceptional absorbency. Furthermore, because the interconnectedness of the cavities in the microbead allows liquids to flow through the microbead, the microbead provides an excellent substrate for use in biotechnology applications such as, for example, chromatographic separation of proteins and peptide synthesis.

The average diameter of the microbead typically ranges from about 5 μm to about 5 mm. Preferred average diameters range from about 50 μm to about 500 μm. This small size facilitates efficient washing of the microbead to remove residual unpolymerized emulsion components. Also, the process of the present invention can be used to produce microbeads of a relatively uniform size and shape, which allows the wash conditions to be optimized to ensure that each microbead in a batch has been thoroughly washed. Thus, the microbead, unlike the prior art HIPE blocks, can be washed with relative ease. This feature of the present invention facilitates cost-efficient scale-up of NIPE polymer production.

An additional feature of the microbead is that the microbead is "skinless" such that some interior cavities and pores communicate with the surface of the microbead. Thus, the microbead offers the advantage over prior art HIPE polymers that a porous polymeric material can be produced directly upon polymerization, obviating the need for a skin-removal step.

The high porosity of the microbead renders it useful as an absorbent material and also as a solid support in a variety of biotechnology applications, including chromatographic separations, solid phase synthesis, immobilization of antibodies or enzymes, and cell culture. Moreover, many of the physical characteristics of the microbead, such as void volume and cavity size, are controllable. Therefore, different types of microbeads, specialized for different uses, can be produced. A description of the general process for producing the microbead is presented below, followed by a discussion of modifications for producing specialized microbeads.

Definitions

The term "microbeads" refers to a crosslinked porous polymeric material wherein at least about 10% of this material consists of substantially spherical and/or substantially ellipsoidal beads. Preferably at least about 20% and more preferably at least about 50% of this material consists of substantially spherical and/or substantially ellipsoidal beads.

As applied to the components of a HIPE, the phrase "substantially water-insoluble" indicates that any component present in the aqueous phase is present at such a low concentration that polymerization of aqueous monomer is less than about 5 weight percent of polymerizable monomer.

As used herein, the term "bulk density" refers to the value obtained by dividing the weight of a known volume of microbeads by that volume.

As used herein, the term "void volume" refers to the volume of a microbead that does not comprise polymeric material. In other words, the void volume of a microbead comprises the total volume of the cavities. Void volume is expressed either as a percentage of the total microbead volume or as a volume per gram of microbead material (cc/gm).

As used herein, the term "cavity size", refers to the average diameter of the cavities present in a microbead.

As used herein, the term "porogen" refers to an organic compound that, when included in the oil phase of a HIPE, promotes the formation of pores connecting the cavities in a microbead.

The abbreviation "DVB" refers to "divinylbenzene"; the abbreviation "AIBN" refers to "azoisobisbutyronitrile"; and the abbreviation "PVA" refers to "poly(vinyl alcohol)", which is produced by hydrolysis of poly(vinyl acetate).

Microbead Production

The microbeads of the present invention are conveniently produced from a HIPE, which comprises an emulsion of an aqueous discontinuous phase in an oil phase. Once formed, the HIPE is added to an aqueous suspension medium to form a suspension of HIPE microdroplets in the suspension medium. Polymerization then converts the liquid HIPE microdroplets to solid microbeads.

In one embodiment, a polymerization initiator is present in both the aqueous discontinuous phase of the HIPE and the aqueous suspension medium. A polymerization initiator can optionally be included in the oil phase as well. In another embodiment, polymerization initiator is present only in the oil phase.

Microbead Production Using an Aqueous Phase Polymerization Initiator

Components of the High Internal Phase Emulsion

The relative amounts of the two HIPE phases are, among other parameters, important determinants of the physical properties of the microbead. In particular, the percentage of the aqueous discontinuous phase affects void volume, density, cavity size, and surface area. For the emulsions used to produce preferred microbeads, the percentage of aqueous discontinuous phase is generally in the range of about 70% to about 98%, more preferably about 75% to about 95%, and most preferably about 80% to about 90%.

The oil phase of the emulsion comprises a monomer, a crosslinking agent, and an emulsifier that is suitable for forming a stable water-in-oil emulsion. The monomer component does not differ from that of prior art HIPE polymers and can be any substantially water-insoluble, monofunctional monomer. In one embodiment, the monomer type is a styrene-based monomer, such as styrene, 4-methylstyrene, 4-ethylstyrene, chloromethylstyrene, 4-t-BOC-hydroxystyrene. The monomer component can be a single monomer type or a mixture of types. The monomer component is typically present in a concentration of about 5% to about 90% by weight of the oil phase. The concentration of the monomer component is preferably about 15% to about 50% of the oil phase, more preferably, about 16% to about 38%.

The crosslinking agent can be selected from a wide variety of substantially water-insoluble, polyfunctional monomers. Preferably, the crosslinking agent is difunctional. Suitable cross-linking agents do not differ from those of the prior art and include divinyl aromatic compounds, such as divinylbenzene (DVB). Other types of cross-linking agents, such as di- or triacrylic compounds and triallyl isocyanurate, can also be employed. The crosslinking agent can be a single crosslinker type or a mixture of types. The crosslinking agent is generally present in a concentration of about 1% to about 90% by weight of the oil phase. Preferably, the concentration of the crosslinking agent is about 15% to about 50% of the oil phase. More preferably, the concentration is about 16% to about 38%.

In addition to a monomer and a crosslinking agent, the oil phase comprises an emulsifier that promotes the formation of a stable emulsion. The emulsifier can be any nonionic, cationic, anionic, or amphoteric emulsifier or combination of emulsifiers that promotes the formation of a stable emulsion. Suitable emulsifiers do not differ from those of the prior art and include sorbitan fatty acid esters, polyglycerol fatty acid esters, and polyoxyethylene fatty acids and esters. In one embodiment, the emulsifier is sorbitan monooleate (sold as SPAN 80). The emulsifier is generally present at a concentration of about 4% to about 50% by weight of the oil phase. Preferably, the concentration of the emulsifier is about 10% to about 25% of the oil phase. More preferably, the concentration is about 15% to about 20%.

In a variation of a first embodiment, the oil phase also contains an oil-soluble polymerization initiator and a porogen. The initiator can be any oil-soluble initiator that permits the formation of a stable emulsion, such as an azo initiator. A preferred initiator is azoisobisbutyronitrile (AIBN). The initiator can be present in a concentration of up to about 5 weight percent of total polymerizable monomer (monomer component plus crosslinking agent) in the oil phase. The concentration of the initiator is preferably about 0.5 to about 1.5 weight percent of total polymerizable monomer, more preferably, about 1.2 weight percent.

The porogen of the present invention can be any nonpolymerizing organic compound or combination of compounds that permits the formation of a stable emulsion, provided that the compound is a good solvent for the monomers employed, but a poor solvent for the polymer produced. Suitable porogens include dodecane, toluene, cyclohexanol, n-heptane, isooctane, and petroleum ether. A preferred porogen is dodecane. The porogen is generally present in a concentration of about 10 to about 60 weight percent of the oil phase. The porogen concentration affects the size and number of pores connecting the cavities in the microbead. Specifically, increasing the porogen concentration increases the size and number of interconnecting pores; while decreasing the porogen concentration decreases the size and number of pores. Preferably, the porogen concentration is about 25 to about 40 weight percent of the oil phase. More preferably, the concentration is about 30 to about 35 weight percent.

In the first embodiment, the aqueous discontinuous phase of a HIPE generally comprises a water-soluble polymerization initiator. The initiator can be any suitable water-soluble initiator. Such initiators are well known and include peroxide compounds such as sodium, potassium, and ammonium persulfates; sodium peracetate; sodium percarbonate and the like. A preferred initiator is potassium persulfate. The initiator can be present in a concentration of up to about 5 weight percent of the aqueous discontinuous phase. Preferably, the concentration of the initiator is about 0.5 to about 2 weight percent of the aqueous discontinuous phase.

Components of the Aqueous Suspension Medium

After formation of a HIPE by a process described in greater detail below, the HIPE is added to an aqueous suspension medium to form an oil-in-water suspension. The aqueous suspension medium comprises a suspending agent and, in the first embodiment, a water-soluble polymerization initiator. The suspending agent can be any agent or combination of agents that promotes the formation of a stable suspension of HIPE microdroplets. Typical droplet stabilizers for oil-in-water suspensions include water-soluble polymers such as gelatin, natural gums, cellulose, and cellulose derivatives (e.g., hydroxyethylcellulose) polyvinylpyrrolidone and poly(vinyl alcohol) (PVA). PVA suitable for use as the suspending agent is produced by partial (85–92%) hydrolysis of polyvinyl acetate. Also used are finely-divided, water-insoluble inorganic solids, such as clay, silica, alumina, and zirconia. Two or more different suspending agents can be combined. Indeed, in one embodiment, the suspending agent is a combination of gelatin or PVA (88% hydrolysis) and modified clay or silica particles.

Modified inorganic solid particles are produced by treating the particles with an agent that increases the hydrophobicity of the particles, thus improving the ability of the particles to stabilize the suspension. In one embodiment, the inorganic solid particles are modified by treating them with a surfactant, such as asphaltene, in the presence of a suitable organic solvent. Suitable organic solvents include toluene, heptane, and a mixture of the two. The relative concentrations of the inorganic solid and asphaltene can be varied to produce modified inorganic solids of varying hydrophobicities. One measure of particle hydrophobicity is "contact angle", which reflects how far a particle penetrates into a water phase at an oil-water interface. A contact angle of 90° indicates that the particle resides half in the oil phase and half in the water phase. A contact angle of less than 90° indicates that the particle penetrates further into the water phase, i.e., is more hydrophilic. In the present invention, the hydrophobicity of the inorganic solid particles is adjusted so that the particles promote the formation of a stable suspension. In a preferred variation of this embodiment, the contact angle of the modified inorganic solid particles is about 65°.

The suspending agent can be present in the aqueous suspension medium in any concentration that promotes the formation of a stable suspension, typically about 0.1 to about 10 weight percent of the aqueous suspension medium. For a preferred combination of suspending agents, a stable suspension is obtained with a PVA concentration of about 0.5% to about 5% and a inorganic solid concentration of about 0.05 to about 0.3% by weight of the aqueous suspension medium.

In addition to a suspending agent, the aqueous suspension medium contains a water-soluble polymerization initiator in the first embodiment of the present invention. The presence of an initiator in the suspension medium, as well as in the HIPE microdroplets, accelerates the polymerization reaction. Generally, rapid polymerization is desirable because of the tendency of the suspension to break down over time.

The initiator can be any suitable water-soluble initiator such as those described above for the aqueous discontinuous phase of the HIPE. In a preferred variation of this embodiment, the initiator is potassium persulfate, present in the suspension medium at a concentration of up to about 5 weight percent. More preferably, the concentration of the initiator is about 0.5% to about 2% by weight of the aqueous suspension medium.

Production of a High Internal Phase Emulsion

The first step in the production of a HIPE-based microbead is the formation of a high internal phase emulsion. A HIPE can be prepared by any of the prior art methods, such as, for example, that disclosed in U.S. Pat. No. 4,522,953 (Barby et al., issued Jun. 11, 1985), which has been incorporated herein by reference. Briefly, a HIPE is formed by combining the oil and aqueous discontinuous phases while subjecting the combination to shear agitation. Generally, a mixing or agitation device such as a pin impeller is used.

The extent and duration of shear agitation must be sufficient to form a stable emulsion. As shear agitation is inversely related to cavity size, the agitation can be increased or decreased to obtain a microbead with smaller or larger cavities, respectively. In one embodiment, a HIPE is prepared using a Gifford-Wood Homogenizer-Mixer (Model 1-LV), set at 1400 rpm. At this mixing speed, the HIPE is produced in approximately 5 minutes. In another embodiment, a HIPE is prepared using an air-powered version of the above mixer (Model 1-LAV), with air pressure set at 5–10 psi for approximately 5–10 minutes. The HIPE can be formed in a batchwise or a continuous process, such as that disclosed in U.S. Pat. No. 5,149,720 (DesMarais et al., issued Sep. 22, 1992).

Production of a HIPE Microdroplet Suspension

Once formed, the HIPE is added to the aqueous suspension medium. The HIPE must be added to the suspension medium in an amount and at a rate suitable for forming a suspension of HIPE microdroplets.

As the HIPE is added, the suspension is subjected to sufficient shear agitation to form a stable suspension. To ensure that the microbeads produced are relatively uniform in size, the mixing device used should provide a relatively uniform distribution of agitation force throughout the suspension. As shear agitation is inversely related to microdroplet size, the agitation can be increased or decreased to obtain smaller or larger HIPE microdroplets, respectively. In this manner, one can control the size of the microbead produced upon polymerization.

To produce a stable microdroplet suspension in a 22 liter spherical reactor having baffles or indents, for example, the HIPE is added to the suspension medium dropwise at a flow rate of up to about 500 ml/minute until the suspension comprises up to about 50% HIPE. Agitation can range from about 50 to about 500 rpm when a propeller- or paddle-style impeller with a diameter of approximately 1.5 to 3 inches is used. In one embodiment, the HIPE is added to the suspension medium in the 22 liter reactor at a flow rate of 20 ml/minute until the suspension comprises about 10% HIPE. Agitation of this mixture at about 250 rpm, followed by polymerization, yields microbeads with an average diameter ranging from about 100 to about 160 μm.

Polymerization of HIPE Microdroplets

Once a stable suspension of HIPE microdroplets is obtained, the temperature of the aqueous suspension medium is increased above ambient temperature, and polymerization is initiated. Polymerization conditions vary depending upon the composition of the HIPE. For example, the monomer or monomer mixture and the polymerization initiator(s) are particularly important determinants of polymerization temperature. Furthermore, the conditions must be selected such that a stable suspension can be maintained for the length of time necessary for polymerization. The determination of a suitable polymerization temperature for a given HIPE is within the level of skill in the art. In general, the temperature of the HIPE suspension should not be elevated above 85° C. because high temperatures can cause the suspension to break. Preferably, when AIBN is the oil-soluble initiator and potassium persulfate is the water-soluble initiator, styrene monomers are polymerized by maintaining the suspension at 60° C. overnight (approximately 18 hours).

Washing of the Microbead

The polymerization step converts a HIPE microdroplet to a solid microbead. As discussed above, this microbead is generally washed to remove any residual, unpolymerized components of the HIPE or the suspension medium. The microbead can be washed with any liquid that can solubilize the residual components without affecting the stability of the microbead. More than one cycle of washing may be required. Preferably, the microbead is washed five times with water, followed by acetone extraction for roughly a day in a Soxhlet extractor. The microbead can then be dried in any conventional manner. Preferably, the microbead is air-dried for two days or is dried under vacuum at 50° C. overnight. The resultant microbeads typically have a bulk density of less than about 0.10 gm/ml.

Microbead Production Using an Oil-Phase Initiator

Microbead Components

In a second embodiment, a polymeric microbead can be produced by a method wherein the polymerization initiator is present in the oil phase instead of the aqueous phase. Suitable initiators for this embodiment include oil-soluble initiators, such as AIBN, benzoyl peroxide, lauroyl peroxide, VAZO-type initiators (such as 1,1'-azobis (cyclohexanecarbonitrile, which is sold as VAZO catalyst 88 by Aldrich, Milwaukee, Wis.), and the like.

In this embodiment, sufficient initiator is added to the oil phase to initiate a free radical reaction. Appropriate initiator concentrations for a given microbead preparation can readily be determined by one skilled in the art. Typically, the initiator is present in a concentration of up to about 5 weight percent of total polymerizable monomer (monomer component plus crosslinking agent) in the oil phase. The concentration of the initiator is preferably about 0.5 to about 3.0 weight percent of total polymerizable monomer, more preferably, about 2.2 weight percent.

In addition, the second embodiment requires the use of a stabilizer capable of forming a boundary between the aqueous discontinuous phase of the HIPE and the aqueous suspension medium where these two aqueous media interface in the microdroplet suspension. This phenomenon is analogous to the situation in soap bubbles where a boundary formed by detergent molecules separates air on the inside of the bubble from outside air. The stabilizer reduces water loss from the HIPE microdroplets and helps prevent microdroplet coalescence.

In general, the stabilizer should be a film forming compound that is soluble in organic solvents and sufficiently hydrophilic to stabilize the interface between the aqueous discontinuous phase of the HIPE and the aqueous suspension medium. These characteristics are found in a variety of natural and synthetic polymers that can serve as stabilizers in this embodiment, including cellulose derivatives, such as methyl cellulose and ethyl cellulose, and PVA (less than about 70% hydrolysis). Other suitable stabilizers can be determined empirically by those skilled in the art in accordance with the teachings herein. Preferably, the stabilizer comprises ethyl cellulose.

The stabilizer concentration must be sufficient to reduce water loss from the HIPE microdroplets and reduce microdroplet coalescence. Optimal concentrations vary with HIPE composition and are determined empirically. Suitable stabilizer concentrations typically range from about 0.01% to about 15% by weight of the oil phase. Higher stabilizer concentrations can be employed; however, at concentrations above 15%, the stabilizer is difficult to wash out of the polymerized microbeads. Preferably, the stabilizer concentration is about 0.1% to about 1% of the oil phase, more preferably, about 0.2% to about 0.6%.

If the stabilizer is not soluble in the oil phase, the stabilizer is typically dissolved in an inert solvent, and the resulting solution is added to the oil phase of the HIPE. In addition to solubilizing the stabilizer, the inert solvent acts as a porogen. The inert solvent can be any solvent that is capable of solubilizing the stabilizer and that is miscible in the oil phase of the HIPE. Examples of inert solvents useful in the second embodiment include trichloroethane, toluene, chloroform, and other halogenated solvents, and the like.

Sufficient inert solvent is added to the stabilizer to increase the solubility of the stabilizer to allow mixing of the stabilizer with the oil phase. The inert solvent concentration varies with the stabilizer and oil phase employed, and the determination of a suitable type and concentration of inert solvent to facilitate the mixing of a particular stabilizer with a given oil phase is within the level of skill in the art. Typically, the inert solvent concentration ranges from about 3% to about 60% by weight of the oil phase and, more preferably, from about 10% to about 40%.

Suitable concentrations of monomer, crosslinking agent, and emulsifier are essentially as described above, except that the concentrations of any of these components can be reduced to accommodate the inclusion of the oil-soluble polymerization initiator, stabilizer, and the inert solvent in the oil phase. Thus, typical concentration ranges for these components in the second embodiment are as follows:

| Component | Concentration (weight % of HIPE) |
|---|---|
| Monomer | 4–90 |
| Crosslinker | 1–89 |
| Emulsifier | 3–50 |

Preferred concentrations for each of these components are the same as discussed above for the first embodiment. In addition, a porogen can optionally be included in the oil phase, as described above for the first embodiment. If a porogen is included, the concentrations of monomer, crosslinking agent, and/or emulsifier can be reduced.

The aqueous discontinuous phase and the aqueous suspension medium of the second embodiment differ from those of the first embodiment in that the aqueous discontinuous phase and aqueous suspension medium of the second embodiment do not include a polymerization initiator. In a variation of the second embodiment, the aqueous discontinuous phase consists essentially of water.

The aqueous suspension medium of this embodiment comprises a suspending agent that can be any agent or combination of agents that promotes the formation of a stable suspension of HIPE microdroplets. Examples of suitable suspending agents are discussed above. Natural gums, such as, for example, acacia gum (commercially available from Aldrich Chemical Co., Milwaukee, Wis.), are preferred. The suspending agent can be present in any concentration that promotes the formation of a stable suspension, typically about 1% to about 30% by weight of the aqueous suspension medium. Preferably, the suspending agent concentration is between about 2% to about 15%.

Microbead Preparation

To prepare microbeads according to the second embodiment, an oil phase is prepared by combining the oil-soluble polymerization initiator, stabilizer, and inert solvent with monomer, crosslinking agent, and emulsifier. A HIPE is formed by combining the oil and aqueous discontinuous phases while subjecting the combination to sufficient shear agitation to form a stable emulsion, as described above. Once formed, the HIPE is added to the aqueous suspension medium in an amount and at a rate suitable for forming a suspension of HIPE microdroplets. As the HIPE is added, the suspension is subjected to shear agitation as described above.

After obtaining a stable suspension, polymerization is initiated by raising the temperature. As explained above, polymerization conditions vary depending upon the composition of the HIPE, and the determination of suitable conditions for a given HIPE is within the level of skill in the art. When lauroyl peroxide is the initiator, for example, polymerization is conveniently carried out for 20 hours at 50° C.

Modifications of the Microbead

The microbead is useful for a variety of applications, notably, as an absorbent material and also as a solid support in biotechnology applications. A microbead-based absorbent can be used, for example, to transport solvents, to absorb body fluids, and as an adhesive microcarrier. Biotechnology applications include chromatographic separations, solid phase synthesis, immobilization of antibodies or enzymes, and microbial and mammalian cell culture. The basic microbead can be modified in a variety of ways to produce microbeads that are specialized for particular applications.

Functionalization of the Microbead for Absorption of Acids

A wide variety of ionic and polar functional groups can be added to the microbead to produce a polymeric microbead that can absorb large quantities of acidic liquids. Such microbeads generally have a greater capacity to absorb aqueous and/or organic acids compared with their capacity for the neutral oil methyl oleate. In particular, the ratio of aqueous and/or organic acid to methyl oleate absorption is generally greater than about 1.2. A preferred starting material for producing such a microbead is a microbead that is crosslinked from about 1% to about 50% and has a void volume of greater than about 70% in its solvent swollen state.

The functionalized microbead comprises the structural unit:

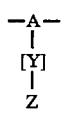

in which A represents a crosslinked carbon chain, Y is an optional spacer group, and Z is an ionic or polar functional group. Z is selected from an amino or substituted amino group and an alkyl cationic ammonium group having eight or more carbon atoms (hereinafter "a higher alkyl") or an alkyl cationic quaternary ammonium group of 8 carbons or less in the presence of an organic counterion having 8 or more carbon atoms. The functionalized microbead can comprise a single type of such structural units or a combination of different types.

In a preferred embodiment, Z is selected from ionic or polar functional groups of structures 1–3:

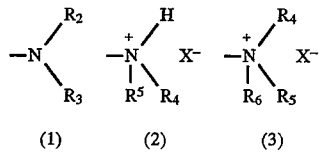

in which $R_2$, $R_3$, $R_4$, $R_5$, and $R_6$ can be the same or different and are selected from an alkyl, cycloalkyl, aryl, and hydroxyalkyl. Alternatively, $R_2$ and $R_3$ can form part of a ring system. When Z is a cationic quaternary ammonium group (3), $R_4$, $R_5$, $R_6$ are preferably selected such that the number of carbons present in $R_4+R_5+R_6$ is 10 or more. When Z is an amine salt group (2), $R_4$ and $R_5$ are preferably selected such that the number of carbons present in $R_4+R_5$ is 8 or more.

The counterion $X^-$ for the cationic quaternary ammonium group (3) or the an amine salt group (2) is an organic or inorganic ion. The counterion for higher alkyl cationic groups is an inorganic species such as chloride, sulfate, or nitrate. Alternatively, the counterion is a long or short chain organic species such as acetate or oleate.

In another embodiment, $R_4$, $R_5$, and $R_6$ are lower alkyl groups such that the number of carbons present in $R_4+R_5+R_6$ is less than 10 for a cationic quaternary ammonium group (3) and the number of carbons present in $R_4+R_5$ is less than 8 for an amine salt (2). In this embodiment, the counterion $X^-$ is preferably an organic group having 8 or more carbons, such as oleate. For a cationic quaternary ammonium group (3), $X^-$ can also be $OH^-$.

The amount of solvent absorbed by the functionalized microbead increases with number of ionic or polar functional groups present, provided the level of crosslinking does not exceed approximately 15–20%. Above this level of crosslinking, the amount of liquid absorbed becomes much less sensitive to the degree of substitution since liquid uptake is then dependent on the mobility of the solvated polymer chains. The level of crosslinking is controlled by altering the relative concentrations of monomer and crosslinker. Preferably, the level of crosslinking is in the range of about 2% to about 10%. The degree of functionalization is generally greater than about 30%, preferably greater than about 50%, and most preferably greater than about 70%.

Functionalized microbeads are produced by the same methods that are used for producing functionalized HIPE polymers. Suitable methods are well known and are disclosed, for example, in U.S. Pat. No. 4,611,014 (Jomes et al., issued Sep. 9, 1986), which is incorporated by reference herein in its entirety. Briefly, the functionalized microbead is generally prepared indirectly by chemical modification of a preformed microbead bearing a reactive group such as bromo or chloromethyl.

A microbead suitable for subsequent chemical modification can be prepared by polymerization of monomers such as chloromethylstyrene or 4-t-BOC-hydroxystyrene. Other suitable monomers are styrene, α-methylstyrene, or other substituted styrene or vinyl aromatic monomers that, after polymerization, can be chloromethylated to produce a reactive microbead intermediate that can be subsequently converted to a functionalized microbead.

Monomers that do not bear reactive groups (including the crosslinking agent) can be incorporated into the microbead at levels up to about 20% or more. To produce HIPE-based microbeads, however, such monomers must permit the formation of a stable HIPE. The concentration of the reactive monomer should generally be sufficiently high to ensure that the functionalized microbead generated after chemical modification bears ionic or polar functional groups on a minimum of about 30% of the monomer residues.

Chemical modification of the reactive microbead intermediate is carried out by a variety of conventional methods. Preferred exemplary methods for producing amine-, amine salt-, and cationic quaternary ammonium-functionalized microbeads are described in detail in Examples 2 to 4, respectively.

In another embodiment, microbeads bearing ionic or polar groups can be prepared directly by emulsification and polymerization of an appropriate substantially water-insoluble monomer.

Functionalization of the Microbead for Absorption of Aqueous Solutions

By selecting different polar or ionic functional groups, the microbead can be functionalized to produce a microbead that absorbs large quantities of aqueous solutions and that also acts as an ion exchange resin. The capacity of these microbeads to absorb a 10% sodium chloride solution is such that the ratio of 10% sodium chloride to water absorption is generally greater than about 0.1, preferably greater than about 0.5, and most preferably greater than about 0.7.

The microbead functionalized for aqueous absorption comprises the structural unit:

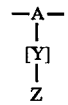

in which A is a crosslinked carbon chain, Y is an optional spacer group, and Z is an ionic or polar functional group. Z is selected from an alkyl cationic ammonium group having ten carbon atoms or less, an alkyl amine salt having eight carbon atoms or less, an alkoxylate, a metal or ammonium or substituted ammonium salt of a sulfuric, carboxylic, phosphoric, or sulfonic acid group, provided that where Z is a sulfonic acid, Y does not have the structure:

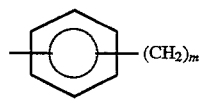

when m = 0

The functionalized microbead can comprise a single type of such structural units or a combination of different types.

In a preferred embodiment, Z is selected from ionic or polar functional groups of structures 1–2:

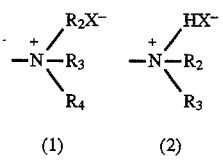

in which $R_2$, $R_3$, and $R_4$ can be the same or different and are selected from an alkyl, cycloalkyl, aryl, and hydroxyalkyl. Alternatively, $R_2$ and $R_3$ form part of a ring system. When Z is a cationic quaternary ammonium group (1), $R_2$, $R_3$, $R_4$ are preferably selected such that the number of carbons present in $R_2+R_3+R_4$ is less than 10. When Z is an amine salt group (2), $R_2$ and $R_3$ are preferably selected such that the number of carbons present in $R_2+R_3$ is less than 8.

The counterion $X^-$ for the cationic quaternary ammonium group (1) or the amine salt group (2) is an inorganic species such as chloride, sulfate, or nitrate. Alternatively, the counterion can be a carboxylate species having less than 8 carbon atoms, such as acetate or lactate. For a cationic quaternary ammonium group (1), $X^-$ can also be $OH^-$.

In one embodiment, Z is an alkoxylated chain of the type:

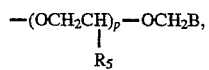

where p is 1 to 680, and

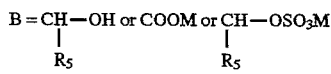

and where $R_5$ is a hydrogen or an alkyl group and M is a metal, an ammonium, or a substituted ammonium cation. Especially preferred is $R_5$=hydrogen, B=$CH_2OH$, and p<20.

Methods for adding the above-described functional groups to HIPE polymers are disclosed in U.S. Pat. No. 4,612,334 (Jones et al., Sep. 16, 1986), which is incorporated by reference herein in its entirety. Microbeads functionalized for aqueous absorption are produced by the same methods that are used for producing the corresponding functionalized HIPE polymers. Suitable methods are the same as those described above for producing microbeads functionalized for acid absorption for functional groups of the same basic type (e.g., amine salts).

In particular, suitable monomers for producing a reactive microbead intermediate that can be functionalized for absorption of aqueous solutions include chloromethylstyrene, n-butyl methacrylate, t-butyl acrylate, 2-ethylhexyl acrylate, or other appropriate acrylate or methacrylate esters. Additionally, monomers such as styrene, α-methylstyrene, or other substituted styrenes or vinyl aromatic monomers can be polymerized and then chloromethylated, sulfonated, nitrated, or otherwise activated to produce a reactive microbead intermediate which can be subsequently converted to a functionalized microbead. Preferred exemplary methods for producing amine salt-, cationic quaternary ammonium-, alkoxylate, and sulfonate salt-functionalized microbeads are described in detail in Examples 5 to 8, respectively.

Production of a Stable Carbon Structure from the Microbead

A microbead can be converted to a porous carboniferous material that retains the original structure of microbead cavities and interconnecting pores. This material is useful, for example, as a sorption or filtration medium and as a solid support in a variety of biotechnology applications (described further in the next section). In addition, the carboniferous microbead can be used as an electrode material in batteries and super-capacitors. Battery electrode materials preferably have a large lattice spacing, such as that of the microbead. A large lattice spacing reduces or eliminates lattice expansion and contraction during battery operation, extending battery cycle lifetimes. Super-capacitors require highly conductive electrodes. The microbead is ideally suited for this application because the interconnectedness of the microbead renders it highly conductive.

To produce a carboniferous microbead, a stable microbead is heated in an inert atmosphere as disclosed for HIPE polymers in U.S. Pat. No. 4,775,655 (Edwards et al., issued Oct. 4, 1988), which is incorporated herein by reference in its entirety. The ability of the microbead to withstand this heat treatment varies depending on the monomer or monomers used. Some monomers, such as styrene-based monomers, yield microbeads that must be stabilized against de-polymerization during heating.

The modification required to stabilize such microbeads can take many forms. Microbead components and process conditions can be selected to achieve a high level of cross-linking or to include chemical entities that reduce or prevent depolymerization under the heating conditions employed. Suitable stabilizing chemical entities include the halogens; sulfonates; and chloromethyl, methoxy, nitro, and cyano groups. For maximum thermal stability, the level of cross-linking is preferably greater than about 20% and the degree of any other chemical modification is at least about 50%. Stabilizing entities can be introduced into the microbead after its formation or by selection of appropriately modified monomers.

Once stabilized, the microbead is heated in an inert atmosphere to a temperature of at least about 500° C. To reduce the stabilizer content of the final carboniferous structure, the temperature should generally be raised to at least about 1200° C. A preferred exemplary method for producing a stable carbon structure from the microbead is described in detail in Example 9.

Production of a Microbead for Use as a Substrate

Many chromatographic and chemical synthesis techniques employ a substrate. In chromatographic separations, components of a solution are separated based on the ability of such components to interact with chemical groups linked to the substrate surface. In solid phase synthesis, the substrate serves as a platform to which a growing molecule, such as a polypeptide, is anchored.

Both processes can be carried out in a batchwise or continuous manner. In batchwise processes, the substrate is contained in a vessel, and solutions comprising components to be separated or reactants are sequentially added and removed by filtration and washing. Alternatively, in continuous or semicontinuous processes, the substrate is contained in a column and solutions are sequentially passed through the column.

The microbead is uniquely suited for use in such systems because the microbead provides a rigid framework that ensures open channels for liquid flow and permits solution components or reactants to diffuse in and out of the microbead. If desired for a particular application, the microbead can be functionalized by providing chemical groups at the microbead surface that interact directly with components or reactants in a solution. Alternatively, the chemical groups at the microbead surface can serve as anchors for other reactive species, such as catalysts, enzymes, or antibodies.

The following sections describe the use of the microbead in chromatography and solid phase synthesis and discuss, as exemplary, the functionalization of the microbead for use in ion-exchange chromatography and peptide synthesis. The discussions of these two applications are intended to be illustrative and do not limit the invention in any way. Variations of these applications will be readily apparent to one skilled in the art and are included within the scope of the invention.

Functionalization of the Microbead for Use in Chromatography

The microbead is useful as a substrate in a variety of chromatographic techniques, including ion-exchange, gel filtration, adsorption, and affinity chromatography.

In ion-exchange chromatography, the components of a mixture are separated in the basis of differences in net charge. Substrates that separate cations, termed "cation-exchange resins", are characterized by the presence of negatively charged groups. Conversely, substrates that separate anions, termed "anion-exchange resins", are characterized by the presence of positively charged groups. A component that binds to an anion-exchange resin, for instance, is typically released from the resin by increasing the Ph of the column buffer or adding anions that compete with the component for binding to the column. Such a component elutes from the column ahead of components having a higher net negative charge and behind components having a lower net negative charge.

Cation-exchange resins can be produced from microbeads by providing acidic groups on the microbead surfaces. Suitable groups include the strongly acidic sulfonate group as well as the weakly acidic carboxylate, carboxymethyl, phosphate, sulfomethyl, sulfoethyl, and sulfopropyl groups. Artion-exchange resins can be produced from microbeads by functionalizing the microbeads with basic groups ranging from the strongly basic quaternary ammoniums to weakly basic groups such as the aminoethyl, diethyaminoethyl, guanidoethyl, and epichlorhydrintriethanolamine groups.

Acidic or basic groups can be added to a preformed microbead as described above for functionalization of the microbead for absorption of acidic and aqueous solutions or by any other conventional method. Alternatively, a microbead bearing such groups can be prepared directly by polymerization of an appropriate monomer.

Regardless of the preparation method, the microbead functionalized for chromatography generally has a void volume of at least about 70% and a cavity size of up to about 50 µm. Preferably microbead has a void volume of about 70% to about 80%. This combination of features ensures rapid uptake of fluids, with relatively unobstructed flow through the microbead.

The capacity of the microbead substrate can be increased by adding a gel to the microbead according to the methods disclosed in U.S. Pat. No. 4,965,289 (Sherrington, issued Oct. 23, 1990). As discussed further in the next section, the gel is formed in or added to the microbead cavities and is linked to the microbead surface. The gel bears either acidic or basic groups, depending on whether the microbead substrate is to serve as an anion-exchange resin or a cation-exchange resin, respectively.

Functionalization of the Microbead for Use in Solid Phase Synthesis

The microbead is functionalized for use in solid phase synthesis by providing chemical groups linked to the microbead surfaces. The chemical groups are selected to interact with one of the reactants involved in the synthesis. Based on the chemical group selected, microbead substrates can be specialized for chemical syntheses of species as diverse as peptides, olignucleotides, and oligosaccharides. Methods for adding appropriate chemical groups to functionalize the microbead for use in such syntheses do not differ from methods previously described for prior art HIPEs and other polymers.

A microbead can be functionalized for peptide synthesis, for instance, as disclosed for HIPE polymers in U.S. Pat. No. 4,965,289 (Sherrington, issued Oct. 23, 1990), which is incorporated herein by reference in its entirety. Briefly, a microbead is prepared such that the void volume is at least about 70% and the cavity size is up to about 50 µm. The microbead is preferably sufficiently cross-linked so that the microbead does not swell to more than twice its dry volume during use.

The chemical group linked to the microbead surface can be any group that binds to the first reactant in the synthesis. In peptide synthesis, for instance, the chemical group is any group that binds the first amino acid of the peptide to be produced. The chemical group should be selected such that the chemical group binds at a position on the amino acid other than the amine group. Typically, the chemical group comprises an amine that reacts with the carboxyl group of the first amino acid.

Chemical groups can be added to a preformed microbead or, alternatively, a microbead bearing chemical groups can be prepared directly by emulsification and polymerization of an appropriate substantially water-insoluble monomer. If desired, chemical groups can be further modified to provide spacer groups that interact with the first amino acid of the peptide.

Peptide synthesis is initiated by binding the first amino acid to suitable chemical groups on the microbead surface. The amine groups of the amino acid reactants are generally protected, and thus chain elongation occurs by alternating rounds of deprotection and coupling of amino acids. The process is terminated by detachment of the peptide from the substrate, after which the peptide is typically purified.

The capacity of the microbead substrate can be increased by adding a gel to the microbead according to the methods disclosed in U.S. Pat. No. 4,965,289 (Sherrington, issued Oct. 23, 1990). Briefly, a suitable microbead is prepared as described above, and a gel or pre-gel is deposited and retained within the microbead cavities. The gel is generally a highly solvent-swollen, cross-linked gel and can, for example, be a soft deformable polyamide gel. For synthetic applications, the gel is generally adapted to interact with a reactant in the synthesis. The ratio of swollen gel to porous material can range from about 60:40 to about 95:5

(weight:weight) and is more preferably from about 75:25 to about 95:5. The most preferred ratio is about 80:20.

The gel can be deposited and retained in the pre-formed microbead by any of the prior art methods for producing gel-filled HIPE polymers, such as those disclosed in U.S. Pat. No. 4,965,289 (Sherrington, issued Oct. 23, 1990), for example. In one embodiment, the gel is formed from pre-gel materials within the microbead cavities. Most preferably, the gel is retained or anchored in the microbead cavities during gel formation. The gel can be retained by chain entanglement and/or interpenetration between the gel and the microbead surfaces. In addition, the gel can be retained by a process that is believed to involve chemical binding between the gel and the microbead surfaces. Combinations of the above mechanisms are also possible.

In one embodiment, the microbead is contacted with a solution comprising pre-gel components and a swelling solvent for the microbead. As the pre-gel components permeate the microbead and begin to form a gel, the microbead swells, entrapping portions of the forming gel by polymer chain interpenetration between the swollen polymeric material of the microbead and the forming gel. Suitable swelling solvents depend on the nature of the microbead polymer and can be readily determined by one skilled in the art. The details of a preferred exemplary method for producing a gel-filled microbead by polymer chain entanglement are set forth in Example 10.

In another embodiment, retention by chemical bonding can be achieved by reacting the gel or pre-gel components with anchor groups on the microbead. Suitable gel anchor groups do not differ from those known in the art, including groups that have double bonds available for interaction with a gel or pre-gel components. Such anchor groups can be introduced into the microbead by modification after microbead formation or by selection of appropriately modified monomers.

For example, a gel-filled microbead can be produced by reacting an amino methyl-functionalized microbead with acryloyl chloride to produce an acrylated microbead. Upon heating in the presence of pre-gel components to initiate gel polymerization, the double bonds of the acrylate group are believed to interact with the forming gel, resulting in covalent linkage of the gel to the microbead. When an acrylated microbead is employed, suitable pre-gel monomers include, for example, acryloyl tyramine acetate and acryloyl sarcosine methyl ester. As discussed above, anchor groups can be introduced into the microbead by modification after microbead formation or by selection of appropriately modified monomers.

Use of the Microbead for Immobilizing Molecules

The microbead can be used as a substrate for a wide variety of molecules including polypeptides and oligonucleotides. The microbead is particularly useful for immobilizing antibodies, lectins, enzymes, and haptens. Methods for attaching such molecules to polymeric substrates are well known. (See, e.g., Tijssen, P. *Laboratory Techniques in Biochemistry and Molecular Biology: Practice and Theories of Enzyme Immunoassays* New York: Elsevier (1985), at pages 298–314.) Several such methods are briefly described below. The methods are described as exemplary and are not intended to be limiting, as one skilled in the art can readily determine how to use or modify these prior art methods to attach a molecule of interest to the microbead.

A polypeptide can be attached to the microbead via non-covalent adsorption or by covalent bonding. Non-covalent adsorption is generally attributed to non-specific hydrophobic interactions and is independent of the net charge of the polypeptide. A polypeptide is attached to the microbead by treating the microbead with a buffer solution containing the polypeptide. Suitable buffers include 50 Mm carbonate, pH 9.6; 10 mM Tris-HCL, pH 8.5, containing 100 mM sodium chloride; and phosphate buffered saline. Polypeptide concentration is generally between 1 and 10 μg/ml. The microbead is typically incubated in this solution overnight at 4° C. in a humid chamber. Polypeptide adsorption levels can be increased by partial denaturation of the polypeptide, for example, by exposing the polypeptide to high temperature, low pH (e.g., 2.5), or denaturants (e.g., urea).

A number of different methods are available for the covalent attachment of polypeptides to the microbead. Conveniently, a polypeptide having a free amino group can be attached to a styrene-based microbead, for example, by treating the microbead with glutaraldehyde at low pH. The polypeptide is then added and the pH of the solution is increased to between about 8.0 and about 9.5 with 100 mM carbonate. The increase in pH increases the reactivity of the glutaraldehyde which binds the polypeptide to the microbead surface. Ethylchloroformate can be substituted for or used in combination with glutaraldehyde in the above procedure.

Alternatively, the microbeads can be functionalized for covalent attachment of polypeptides. Such a microbead provides anchor groups that bind to the polypeptide of interest. Suitable anchor groups for attaching polypeptides to polymers are well known and include hydrazide groups, alkylamine groups, and Sanger's reagent. Anchor groups can be introduced into the microbead by modification after microbead formation or by selection of appropriately modified monomers.

In addition, a polypeptide can be attached to the microbead via a bridging molecule. This method of attachment is useful for polypeptides that bind poorly to the microbead. Such polypeptides are conjugated to a bridging molecule that has a high affinity for plastic, such as, for example, bovine serum albumin (BSA). To attach a polypeptide to a microbead via a BSA bridge, BSA is added to the microbead, and then the polypeptide is conjugated to the immobilized BSA using a conventional crosslinker such as a carbodiimide.

In another embodiment, the microbead serves as a substrate for an oligonucleotide. Conveniently, the oligonucleotide can be adsorbed to a microbead by treating the microbead with a polycationic substance such as methylated BSA, poly-L-lysine, or protamine sulfate. When the latter is used, the microbead is typically treated for about 90 minutes with a 1% aqueous solution of protamine sulfate, followed by several distilled water washes. The microbead is then allowed to dry. An oligonucleotide is adsorbed onto the treated microbead by adding the oligonucleotide to the microbead at a concentration of about 10 μg/ml in a buffer such as 50 mM Tris-HCl, pH 7.5, containing 10 mM ethylenediaminetetraacetic acid (EDTA) and 10 mM ethylene glycol-bis(β-amino ethyl ether)N,N,N',N'-tetracetic acid (EGTA). Generally, a treatment time of 60 minutes provides suitable results.

Use of the Microbead in High Density Cell Culture

In addition to the above applications, the microbead is also useful in cell culture. High density cell culture generally requires that cells be fed by continuous perfusion with growth medium. Suspension cultures satisfy this requirement, however, shear effects limit aeration at high cell concentration. The microbead protects cells from these shear effects and can be used in conventional stirred or airlift bioreactors.

To prepare a microbead for use in culturing eukaryotic or prokaryotic cells, the microbead is generally sterilized by any of the many well-known sterilization methods. Suitable methods include irradiation, ethylene oxide treatment, and, preferably, autoclaving. Sterile microbeads are then placed in a culture vessel with the growth medium suitable for the cells to be cultured. Suitable growth media are well known and do not differ from prior art growth media for suspension cultures. An inoculum of cells is added and the culture is maintained under conditions suitable for cell attachment to the microbeads. The culture volume is then generally increased, and the culture is maintained in the same manner as prior art suspension cultures.

Microbeads can be used in cell culture without modification, however, the microbeads can also be modified to improve cell attachment, growth, and the production of specific proteins. For instance, a variety of bridging molecules can be used to attach cells to the microbeads. Suitable bridging molecules include antibodies, lectins, glutaraldehyde, and poly-L-lysine. In addition, sulfonation of microbeads, as described above, increases cell attachment rates. Example 11 illustrates the use sulfonated microbeads in an exemplary mammalian cell culture.

This invention is further illustrated by the following specific but non-limiting examples. Procedures that are constructively reduced to practice are described in the present tense, and procedures that have been carried out in the laboratory are set forth in the past tense.

EXAMPLE 1

A. Microbead Production Using Aqueous- and Oil-Phase Initiators

Exemplary preferred microbeads were prepared according to the following protocol. The final concentration of each component of the HIPE and the aqueous suspension medium is shown in Table 1, Study 4. Table 1 also shows studies in which the following protocol was varied as indicated. The results of these studies are set forth in Table 2.

1. Prepare an oil phase by combining 11.37 gm styrene-based monomer, 11.25 gm DVB, 8.00 gm span 80, 0.27 gm AIBN; and 15.00 gm dodecane with stirring at room temperature.

2. Prepare an aqueous discontinuous phase by adding 0.78 gm potassium persulfate to 94.3 ml of distilled water.

3. Stir the oil phase at approximately 1400 rpm, and then add the aqueous discontinuous phase to the oil phase at a flow rate of 20 ml/minute. Stir the combined phases at 1400 rpm for approximately 5–10 minutes to form a stable HIPE.

4. Prepare an aqueous suspension medium by combining 2 gm potassium persulfate and 3 gm of Kaolinite clay (Georgia Kaolin Co., Inc.) with 1 liter of distilled water. Stir the mixture at 700 rpm for about 15 minutes, and then adjust the stirring speed to 250 rpm.

5. Add the HIPE to the aqueous suspension medium dropwise at a flow rate of 15 ml/minute in a 22 liter Lurex reactor (Model no. LX6214-1008) until the suspension reaches about 20% HIPE.

6. To form microbeads, polymerize the suspension by raising the temperature to 60° C. overnight (approximately 18 hours) while stirring at 250 rpm.

7. Wash the resultant microbeads five times with water and then perform acetone extraction in a Soxhlet extractor for about a day. Allow the microbeads to air-dry overnight. The bulk density of the resultant material is 0.055 gm/ml of dried microbeads.

B. Microbead Production Using an Oil-Phase Initiator

Exemplary preferred microbeads were prepared according to the following alternative protocol. The final concentration of each component of the HIPE and the aqueous suspension medium is shown in Table 3, Study 7. Table 3 also shows studies in which the following protocol was varied as indicated. The results of these studies are set forth in Table 4.

1. In a 1 liter beaker, prepare an oil phase by dissolving 0.4 gm ethyl cellulose in 30 gm trichloroethane, and adding 20 gm styrene-based monomer, 19.5 gm DVB, 22 gm span 80, and 0.9 gm lauroyl peroxide. Mix the components by stirring at room temperature.

2. Place the beaker under a Gifford-Wood Homogenizer-Mixer (Model 1-LV; commercially available from Greerco, Hudson, NH) and stir at 1800 to 4800 rpm while slowly adding 850 gm deionized water to form a HIPE.

3. In a 2 liter glass cylinder reactor (from Ace Glass, Vineland, N.J.), prepare an aqueous suspension medium by combining 120 gm acacia gum with 800 gm of deionized water. While stirring at 100 rpm, heat the mixture to 60°–70° C. for approximately 15 minutes, and then cool the mixture to about 40° C.

4. Add the HIPE to the aqueous suspension medium dropwise at a flow rate of approximately 200 ml/minute.

5. Adjust the mixing speed to between 10 rpm and 300 rpm, depending on the desired bead size.

6. To form microbeads, polymerize the suspension by raising the temperature to 45° C. for approximately 20 hours under constant stirring.

7. Wash the resultant microbeads five times with water and then perform an acetone extraction followed by a methanol extraction in a Soxhlet extractor for approximately 18 hours each. Allow the microbeads to air-dry overnight.

TABLE 1

Microbead Production Using Aqueous- and Oil-Phase Initiators

| No. | Monomer (type)/ (wt % in HIPE) | Cross-linker (type)/ (wt % in HIPE) | Emulsifier (type)/ (wt % in HIPE) | Porogen* (type)/ (wt % in HIPE) | Mixing speed - HIPE formation (rpm) | Volume of water in HIPE** (ml)/(%) | Suspending agent*** (type)/ (wt % in water) | Mixing speed - Suspension (rpm) | Polymer, temp. (°C.) |
|---|---|---|---|---|---|---|---|---|---|
| 1 | Styrene/ 27 | DVB#/ 25 | Span 80/ 17 | Dodecane/ 33 | 725 | 435.0/91 | PVA/3 | 250 | 60 |
| 2 | Styrene/ 25 | DVB/ 25 | Span 80/ 17 | Dodecane/ 33 | 1400 | 435.0/91 | PVA/3 + Clay (90°)/ 0.2 | 250 | 60 |
| 3 | Styrene/ 25 | DVB/ 25 | Span 80/ 17 | Dodecane/ 33 | 1400 | 435.0/91 | Gelatin/2 | 250 | 60 |

TABLE 1-continued

Microbead Production Using Aqueous- and Oil-Phase Initiators

| No. | Monomer (type)/ (wt % in HIPE) | Cross-linker (type)/ (wt % in HIPE) | Emulsifier (type)/ (wt % in HIPE) | Porogen* (type)/ (wt % in HIPE) | Mixing speed - HIPE formation (rpm) | Volume of water in HIPE** (ml)/(%) | Suspending agent*** (type)/ (wt % in water) | Mixing speed - Suspension (rpm) | Polymer, temp. (°C.) |
|---|---|---|---|---|---|---|---|---|---|
| 4 | Styrene/ 25 | DVB/ 25 | Span 80/ 17 | Dodecane/ 33 | 1400 | 94.3/70 | Clay (90°)/ 0.3 | 250 | 60 |
| 5 | Styrene/ 25 | DVB/ 25 | Span 80/ 17 | Dodecane/ 33 | 1400 | 94.5/70 | Triton X-100/ 0.5 | 200 | 60 |
| 6 | Styrene/ 25 | DVB/ 24 | Span 80/ 17 | Dodecane/ 33 | 1400 | 184.0/82 | PVA/0.5 Clay (65°)/ 0.3 | 250 | 60 |
| 7 | Styrene/ 25 | DVB/ 24 | Span 80/ 17 | Dodecane/ 33 | 1400 | 184.0/82 | Gelatin/2 Clay (65°)/ 0.3 | 250 | 60 |
| 8 | Styrene/ 24 | DVB/ 24 | Span 80/ 17 | Dodecane/ 34 | 1400 | 184.0/82 | Gelatin/2.5 | 250 | 65 |
| 9 | Styrene/ 24 | DVB/ 24 | Span 80/ 17 | Dodecane/ 34 | 1400 | 110.0/72 | Gelatin/2 + Silica (65°)/0.3 | 250 | 65 |
| 10 | Styrene/ 24 | DVB/ 24 | Span 80/ 17 | Dodecane/ 34 | 2800 | 94.3/70 | Gelatin/2.5 | 250 | 65 |
| 11 | Styrene/ 24 | DVB/ 24 | Span 80/ 17 | Dodecane/ 34 | 1400 | 94.3/70 | Gelatin/2 + Silica (65°)/0.3 | 300 | 65 |
| 12 | Styrene/ 24 | DVB/ 24 | Span 80/ 17 | Dodecane/ 34 | 1400 | 94.3/70 | Gelatin/2 + Silica (65°)/0.3 | 400 | 65 |
| 13 | Styrene/ 4 | DVB/ 24 | Span 80/ 17 | Dodecane/ 34 | 1400 | 94.3/70 | Gelatin/2 + Silica (65°)/0.3 | 450 | 65 |
| 14 | Styrene/ 24 | DVB/ 24 | Span 80/ 17 | Dodecane/ 34 | 1400 | 94.3/70 | Gelatin/1.5 | 250 | 65 |
| 15 | Styrene/ 40 | DVB/ 9 | Span 80/ 17 | Dodecane/ 34 | 1400 | 94.3/70 | Gelatin/1.5 | 250 | 65 |
| 16 | ST-CH$_2$Cl##/ 24 | DVB/ 24 | Span 80/ 17 | Dodecane/ 34 | 1400 | 94.3/70 | Gelatin/2 | 250 | 65 |
| 17 | Styrene/ 13 | DVB/ 35 | Span 80/ 17 | Dodecane/ 34 | 1400 | 94.3/70 | Gelatin/0.8 | 250 | 65 |
| 18 | Styrene/ 13 | DVB/ 35 | Span 80/ 17 | Dodecane/ 34 | 1400 | 794.2/95 | Gelatin/2 + Silica (65°)/0.3 | 200 | 65 |
| 19 | Styrene/ 45 | DVB/ 4 | Span 80/ 17 | Dodecane/ 34 | 1400 | 94.3/70 | Gelatin/2 + Silica (65°)/0.3 | 200 | 65 |
| 20 | Styrene/ 13 | DVB/ 35 | Span 80/ 17 | Dodecane/ 34 | 1400 | 184.0/82 | Gelatin/2 + Silica (65°)/0.3 | 300 | 65 |

*The oil phase also contained 1.2 wt % azoisobisbutyronitrile (wt % of total polymerizable monomer).
**The aqueous discontinuous phase contained 0.8 gm potassium persulfate, for final concentrations ranging between 0.1 and 0.8 wt. %.
***The suspension medium also contained 0.07 wt % potassium persulfate.
Purity = 55%
ST-CH$_2$Cl = choromethylated styrene

TABLE 2

Properties of Microbeads from Table 1 Studies

| No. | Microbead Size* | Microbead Density | Cavity Size |
|---|---|---|---|
| 1 | 100 μm–300 μm | <0.04 gm/ml | >10 μm |
| 2 | 100 μm–300 μm | <0.04 gm/ml | 5–10 μm |
| 3 | 100 μm–300 μm | <0.04 gm/ml | 5–10 μm |
| 4 | 200 μm–3 mm | 0.06–0.07 gm/ml | 5–10 μm |
| 5 | 200 μm–3 mm | 0.06–0.07 gm/ml | 5–10 μm |
| 6 | 200 μm–3 mm | 0.04–0.05 gm/ml | 5–10 μm |
| 7 | 100 μm–300 μm | 0.04–0.05 gm/ml | 5–10 μm |
| 8 | 100 μm–300 μm | 0.04–0.05 gm/ml | 5–10 μm |
| 9 | 100 μm–300 μm | 0.06–0.07 gm/ml | 5–10 μm |
| 10 | 100 μm–300 μm | 0.06–0.07 gm/ml | <2 μm |
| 11 | 50 μm–180 μm | 0.06–0.07 gm/ml | 5–10 μm |
| 12 | 20 μm–100 μm | 0.06–0.07 gm/ml | 5–10 μm |
| 13 | 20 μm–100 μm | 0.06–0.07 gm/ml | 5–10 μm |
| 14 | 200 μm–3 mm | 0.06–0.07 gm/ml | 5–10 μm |
| 15 | 200 μm–3 mm | 0.06–0.07 gm/ml | 5–10 μm |
| 16 | 100 μm–300 μm | 0.06–0.07 gm/ml | 5–10 μm |
| 17 | 200 μm–3 mm | 0.06–0.07 gm/ml | 5–10 μm |
| 18 | 100 μm–300 μm | Not determined | 5–10 μm |
| 19 | 100 μm–300 μm | 0.06–0.07 gm/ml | 5–10 μm |
| 20 | 50 μm–180 μm | 0.04–0.05 gm/ml | 5–10 μm |

*Microbead yield for each experiment was 75–85%.

TABLE 3

Microbead Production Using an Oil-Phase Initiator

| No. | Monomer (type)/ (wt % in HIPE) | Cross-linker (type)/ (wt % in HIPE) | Emulsifier and Stabilizer (type)/ (wt % in HIPE) | Inert Solvent (type)/ (wt % in HIPE) | Mixing speed - HIPE formation (rpm) | Volume of water in HIPE (%) | Suspending agent (type)/ (wt % in water) | Mixing Speed - Suspension (rpm) | Polymer. temp. (°C.) | Ratio HIPE phase/ suspension medium (g/g) |
|---|---|---|---|---|---|---|---|---|---|---|
| 1 | Styrene/ 34.23 | DVB/ 31.39 | Span 80/25.65 Ethyl Cellulose/0.69 | TCE/ 8.04 | 2800 | 87.60 | Acacia/ 7.4 | 120 | 50 | 536.3/ 1080 |
| 2 | Styrene/ 19.39 | DVB/ 19.09 | Span 80/13.16 Ethyl Cellulose/0.30 | TCE/ 48.06 | 3100 | 79.90 | Acacia/ 5.66 | 120 | 50 | 312.88/ 530 |
| 3 | Styrene/ 19.18 | DVB/ 17.56 | Span 80/15.67 Ethyl Cellulose/0.38 | TCE/ 47.56 | 3200 | 78.50 | Acacia/ 3.84 | 100 | 53 | 299.35/ 520 |
| 4 | Styrene/ 26.00 | DVB/ 23.38 | Span 80/17.28 Ethyl Cellulose/0.45 | TCE/ 32.47 | 2800 | 86.58 | Acacia/ 9.90 | 150 | 50 | 693/ 1110 |
| 5 | Styrene/ 20.59 VBC/ 5.41 | DVB/ 23.82 | Span 80/17.28 Ethyl Cellulose/0.45 | TCE/ 32.46 | 3100 | 86.58 | Acacia/ 9.90 | 150 | 47 | 692.98/ 1110 |
| 6 | Styrene/ 25.65 | DVB/ 23.55 | Span 80/18.24 Ethyl Cellulose/0.40 | TCE/ 32.16 | 4800 | 89.93 | Acacia/ 10.71 | 120 | 45 | 933.98/ 1120 |
| 7 | Styrene/ 21.79 | DVB/ 21.17 | Span 80/23.95 Ethyl Cellulose/0.41 | TCE/ 32.68 | 4800 | 90.14 | Acacia/ 13.04 | 200 | 45 | 942.93/ 920 |

Note:
1. The oil phase contained approximately 2 wt % lauroyl peroxide (wt % of total polymerizable monomer).
2. The aqueous discontinuous phase is water.
3. VBC = vinylbenzyl chloride.
4. TCE = 1,1,1-trichloroethane.

TABLE 4

Properties of Microbeads from Table 3 Studies

| No. | Approximate Bulk Density (g/ml) | Microbead Size* Range (µm) |
|---|---|---|
| 1 | 0.15 | 100–200 |
| 2 | 0.12 | 80–200 |
| 3 | 0.14 | 150–400 |
| 4 | 0.13 | 50–150 |
| 5 | 0.15 | 50–150 |
| 6 | 0.09 | 100–300 |
| 7 | 0.10 | 30–150 |

*Microbead yield for each experiment was approximately 85–95%.

EXAMPLE 2

Functionalization of Microbeads for Absorption of Acids Using Amine Groups

Diethylamine-functionalized microbeads are produced from chloromethylstyrene microbeads prepared as described in Example 1. The microbeads are air-dried overnight and Soxhlet extracted for 15 hours with 200 ml hexane to remove residual unpolymerized components. 5 gm of microbeads are then refluxed with 150 ml aqueous diethylamine for 20 hours. The resultant diethylamine-functionalized microbeads are 85% substituted and have a capacity of 1.5 mM/gm. 1 gm of this material absorbs 20 ml of 1N sulfuric acid.

EXAMPLE 3

Functionalization of Microbeads for Absorption of Acids Using Amine Salts

To produce a dihexylammonium salt, dihexylamine-functionalized microbeads are prepared as described above in Example 3 for diethylamine-functionalized microbeads. 1 gm dihexylamine-functionalized microbeads are then added to 100 ml methanolic HCl and stirred for 30 minutes. The counterion of the resultant salt is chloride. The dihexylammonium chloride-functionalized microbeads are collected by filtration, washed with 3 times with 50 ml methanol, and air-dried overnight. The resultant microbeads are 70% substituted.

EXAMPLE 4

Functionalization of Microbeads for Absorption of Acids Using Quaternary Ammonium Groups To produce a dimethyldecylammonium salt, chloromethylstyrene microbeads are prepared as described in Example 1. The microbeads are air-dried overnight and Soxhlet extracted with hexane to remove residual unpolymerized components. 1 gm microbeads are then filled under vacuum with a 10-fold molar excess of ethanolic amine and refluxed for 7 hours. The counterion of the resultant salt is chloride. The dimethyldecylammonium chloride-functionalized microbeads are collected by filtration, washed twice with 50 ml ethanol and twice with 50 ml methanol, and then air-dried overnight. The resultant microbeads are 70% substituted.

EXAMPLE 5

Functionalization of Microbeads for Absorption of Aqueous Solutions Using Amine Salts To produce a dimethylammonium salt, diethylamine-functionalized microbeads are prepared as described in Example 3. The microbeads are air-dried overnight and Soxhlet extracted with hexane to remove residual unpolymerized components. 1 gm microbeads are then added to 100 ml methanolic HCl and stirred for 30 minutes. The counterion of the resultant salt is chloride. The diethylamine chloride-functionalized microbeads are 85% substituted.

EXAMPLE 6

Functionalization of Microbeads for Absorption of Aqueous Solutions Using Quaternary Ammonium Groups To produce a dimethyldecylammonium salt, chloromethylstyrene microbeads prepared as described in Example 1.

The microbeads are air-dried overnight and Soxhlet extracted with hexane to remove residual unpolymerized components. 1 gm microbeads are then treated with 100 ml aqueous amine for 30 minutes. The resultant dimethyldecylammonium chloride-functionalized microbeads are 85% substituted.

EXAMPLE 7

Functionalization of Microbeads for Absorption of Aqueous Solutions Using Alkoxylate Groups Ethoxylated microbeads are prepared from chloromethylstyrene microbeads prepared as described in Example 1. The microbeads are air-dried overnight and Soxhlet extracted with hexane to remove residual unpolymerized components. 1 gm microbeads are then treated with 100 ml of the anionic form of a polyethylene glycol (PEG) containing 8–9 ethylene glycol monomers in excess PEG as solvent. The reactants are heated at 95° C. for 2 hours. The resultant ethoxylated microbeads are 90% substituted.

EXAMPLE 8

Functionalization of Microbeads for Absorption of Aqueous Solutions Using Sulfonate Groups Sulfonate-functionalized microbeads were produced from styrene microbeads prepared as described in Example 1. The microbeads were dried under vacuum at 50° C. for two days. 10 gm of microbeads were then added to a 500 ml flask containing a mixture of 200 ml of chloroform and 50 ml of chlorosulfonic acid. The flask is shaken at room temperature for two days. The sulfonate-functionalized microbeads are collected by filtration and washed sequentially with 250 ml each of chloroform, methylene chloride, acetone, and methanol. The microbeads are soaked in 300 ml 10% aqueous sodium hydroxide overnight and then washed with water until the eluate reaches neutral pH. The bulk density of the resultant material is 0.067 gm/ml of dried microbeads and the capacity is 2.5 mM/gm. 1 gm of this material absorbs 23.5 gm of water.

EXAMPLE 9

Production of Stable Carbon Structures from Chloromethylstyrene Microbeads 3-chloromethylstyrene microbeads are prepared as described in Example 1 such that the level of crosslinking is between 20–40% and the void volume is 90%. 1 gm microbeads are then placed in an electrically heated tube furnace, and the temperature is increased to 600° C. in an oxygen-free nitrogen atmosphere. The rate of heating is generally maintained below 5° C. per minute, and in the range of 180° C. to 380° C., the rate of heating does not exceed 2° C. per minute. After the heating process, the microbeads are cooled to ambient temperature in an inert atmosphere to prevent oxidation by air.

EXAMPLE 10

Production of Gel-Filled Microbeads for Use as a Substrate for Protein Synthesis Microbeads with a void volume of 90%, a bulk density of 0.047 gm/ml, an average cavity diameter in the range of 1–50 µm, and which are 10% crosslinked are prepared as described in Example 1. The gel employed is poly(N-(2-(4-acetoxyphenyl)ethyl)-acrylamide). To produce a solution of gel precursors, 2.5 gm of monomer, 0.075 gm of the crosslinking agent ethylene bis(acrylamide), and 0.1 gm of the initiator AIBN is added to 10 ml of the swelling agent dichloroethane. The gel precursor solution is then deoxygenated by purging with nitrogen.

0.7 gm of microbeads is added to the gel precursor solution and polymerization is initiated by heating the mixture at 60° C. while rotating the sample on a rotary evaporator modified for reflux. The dichloroethane swells the microbeads, allowing the gel precursors to penetrate the microbead and form a polyamide that becomes interpenetrated with the polymer chains of the microbead. After 1 hour, the gel-filled microbeads (hereinafter "composite") are washed with 50 ml dimethyl formamide (DMF) and 50 ml diethyl ether and then vacuum dried. The yield of composite is 2.7 gm.

To produce chemical groups within the composite, 0.25 gm of the composite is treated with 50 ml of a 5% solution of hydrazine hydrate in DMF for 5 minutes. This treatment provides free phenolic functionalities within the gel matrix that act as chemical groups for peptide synthesis.

EXAMPLE 11

Use of Microbeads in High Density Cell Culture

To produce microbeads suitable for mammalian cell culture, sulfonated microbeads are prepared as described in Example 8 and are then wetted in a 70% ethanol solution and autoclaved at 121° C. for 15 minutes. The microbeads are then washed twice with sterile phosphate-buffered saline and once with complete growth medium. 500 mg of the sterile microbeads are placed in a 500 ml roller bottle that has been siliconized to prevent attachment of the cells to the bottle.

An inoculum of $5 \times 10^7$ baby hamster kidney cells in 50 ml of growth medium (containing 10% fetal calf serum) is added to the roller bottle. The inoculum is incubated with the microbeads for 8 hours at 37° C. with periodic agitation to allow cell attachment to the microbeads. The culture volume is then increased to 100 ml, and the roller bottle is gassed with an air-$CO^2$ (95:5) mixture and placed in a roller apparatus. Growth medium is replaced whenever the glucose concentration drops below 1 gm/liter.

What is claimed is:

1. Porous crosslinked polymeric microbeads having cavities joined by interconnecting pores wherein at least some of the cavities at the interior of each microbead communicate with the surface of the microbead and wherein approximately 10% of the microbeads are substantially spherical or substantially ellipsoidal or a combination thereof.

2. The microbeads of claim 1 wherein the microbeads have an average diameter in the range of about 5 µm to about 5 mm.

3. The microbeads of claim 1 wherein the microbeads have a void volume of at least about 70%.

4. A process for producing a porous, crosslinked polymeric microbead comprising (a) combining
  (i) an oil phase comprising
    (1) a substantially water-insoluble, monofunctional monomer;
    (2) a substantially water-insoluble, polyfunctional crosslinking agent;
    (3) an emulsifier that is suitable for forming a stable water-in-oil emulsion; and
    (4) a stabilizer, wherein said stabilizer is a film-forming compound that is soluble in an organic solvent, and said stabilizer is present in the oil phase at a concentration in the range of about 0.01 to about 15 weight percent; and (ii) an aqueous discontinuous phase to form an emulsion, wherein the emulsion comprises at least about 70% aqueous discontinuous phase;

(b) adding the emulsion to an aqueous suspension medium to form an oil-in-water suspension of dispersed emulsion droplets; and (c) polymerizing the emulsion droplets.

5. The process of claim 4 wherein the monomer comprises a styrene-based monomer.

6. The process of claim 4 wherein the monomer is present in the oil phase at a concentration in the range of about 4 to about 90 weight percent.

7. The process of claim 4 wherein the crosslinking agent comprises an agent selected from the group consisting of a divinylbenzenic compound, a di- or triacrylic compound, and a triallyl isocyanurate.

8. The process of claim 4 wherein the crosslinking agent is present in the oil phase at a concentration in the range of about 1 to about 89 weight percent.

9. The process of claim 4 wherein the emulsifier comprises an agent selected from the group consisting of a sorbitan fatty acid ester, a polyglycerol fatty acid ester, and a polyoxyethylene fatty acid or ester.

10. The process of claim 4 wherein the emulsifier is present in the oil phase at a concentration in the range of about 3 to about 50 weight percent.

11. The process of claim 4 wherein the oil-in-water suspension comprises an amount of high internal phase emulsion suitable for generating a stable suspension.

12. The process of claim 4 wherein the aqueous suspension medium comprises a suspending agent.

13. The process of claim 12 wherein the suspending agent comprises an agent selected from the group consisting of a water-soluble polymer and a water-insoluble inorganic solid.

14. The process of claim 12 wherein the suspending agent comprises a natural gum.

15. The process of claim 12 wherein the suspending agent is present in the aqueous suspension medium at a concentration of about 1 to about 30 weight percent.

16. The process of claim 4 wherein the suspension is formed by adding the high internal phase emulsion to the aqueous suspension medium while providing sufficient shear agitation to generate a stable suspension.

17. The process of claim 4 wherein the oil phase additionally comprises an oil-soluble polymerization initiator, and no polymerization initiator is present in either the aqueous discontinuous phase or the aqueous suspension medium.

18. The process of claim 17 wherein the oil-soluble initiator is selected from the group consisting of AIBN, benzoyl peroxide, lauroyl peroxide, and a VAZO initiator.

19. The process of claim 17 wherein the oil-soluble polymerization initiator is present in the oil phase at a concentration of up to about 5 weight percent of total polymerizable monomer.

20. The process of claim 17 wherein the aqueous discontinuous phase consists essentially of water.

21. The process of claim 17 wherein the stabilizer comprises a natural or synthetic polymeric stabilizer.

22. The process of claim 21 wherein the polymeric stabilizer comprises a cellulose derivative.

23. The process of claim 21 wherein the polymeric stabilizer comprises an agent selected from the group consisting of methyl cellulose, ethyl cellulose, and partially hydrolyzed poly(vinyl alcohol).

24. A process for producing a porous crosslinked polymeric microbead comprising (a) combining
  (i) an oil phase comprising
    (1) styrene;
    (2) divinylbenzene;
    (3) lauroyl peroxide;
    (4) trichloroethane;
    (5) sorbitan monooleate; and
    (6) ethylcellulose; and
  (ii) an aqueous discontinuous phase that does not contain a polymerization initiator to form an emulsion;

(b) adding the emulsion to an aqueous suspension medium to form an oil-in-water suspension of dispersed emulsion droplets, wherein said suspension medium comprises acacia gum and does not contain a polymerization initiator; and (c) polymerizing the emulsion droplets.

25. A porous crosslinked polymeric microbead produced by the process comprising (a) combining
  (i) an oil phase comprising
    (1) styrene;
    (2) divinylbenzene;
    (3) lauroyl peroxide;
    (4) trichloroethane;
    (5) sorbitan monooleate; and
    (6) ethylcellulose; and
  (ii) an aqueous discontinuous phase that does not contain a polymerization initiator to form an emulsion;

(b) adding the emulsion to an aqueous suspension medium to form an oil-in-water suspension of dispersed emulsion droplets, wherein said suspension medium comprises acacia gum and does not contain a polymerization initiator; and (c) polymerizing the emulsion droplets.

26. The process of claim 17 wherein the oil phase additionally comprises a porogen.

27. The microbeads of claim 3 wherein approximately 20% of the microbeads are substantially spherical or substantially ellipsoidal or a combination thereof.

28. The microbeads of claim 27 wherein approximately 50% of the microbeads are substantially spherical or substantially ellipsoidal or a combination thereof.

29. The microbeads of claim 3 wherein the microbeads have an average diameter in the range of about 50 μm to about 500 μm.

30. The microbeads of claim 3 wherein the bulk density of the microbeads is in the range of about 0.05 gm/ml to about 0.2 gm/ml.

31. The microbeads of claim 3 wherein the microbeads have been functionalized such that the functionalized microbeads absorb aqueous and/or organic acidic liquids, said functionalized microbeads comprising the structural unit:

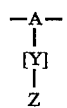

in which
  A is a crosslinked carbon chain;
  Y is an optional spacer group; and
  Z is an ionic or polar functional group.

32. The functionalized microbeads of claim 31 wherein the ratio of aqueous and/or organic acid absorption by the functionalized microbeads to methyl oleate absorption is greater than about 1.2.

33. The functionalized microbeads of claim 31 wherein Z is selected from the group consisting of an amino or substituted amino group;

an alkyl cationic quaternary ammonium group having 8 or more carbon atoms; and an alkyl cationic quaternary ammonium group of 8 carbon atoms or less in the presence of a counterion that is an organic group containing 8 or more carbon atoms.

34. The functionalized microbeads of claim 31 wherein Z comprises an ionic or polar functional group selected from the group consisting of species 1–3:

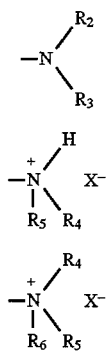

in which $R_2$, $R_3$, $R_4$, $R_5$, and $R_6$ can be the same or different and are selected from the group consisting of an alkyl, cycloalkyl, aryl, hydroxyalkyl; or $R_2$ and $R_3$ form part of a ring system; and the number of carbons present in $R_4+R_5+R_6$ is 10 or more for a cationic quaternary ammonium (3);

the number of carbons present in $R_4+R_5$ is 8 or more for an amine salt (2); and the counterion $X^-$ is an organic or inorganic ion.

35. The functionalized microbeads of claim 34 wherein the number of carbons present in $R_4+R_5+R_6$ is less than 10 for a cationic quaternary ammonium (3);

the number of carbons present in $R_4+R_5$ is less than 8 for an amine salt (2); and the counterion $X^-$ is an organic group having 8 or more carbons.

36. The functionalized microbeads of claim 31 wherein the level of crosslinking is from about 1 to about 20%.

37. The functionalized microbeads of claim 31 wherein the level of crosslinking is from about 2 to about 10%.

38. The functionalized microbeads of claim 31 wherein the void volume of the microbeads is greater than about 80%.

39. The functionalized microbeads of claim 31 wherein the degree of functionalization is greater than about 50%.

40. The microbeads of claim 3 wherein the microbeads have been functionalized such that the functionalized microbeads absorb aqueous liquids, said functionalized microbeads comprising the structural unit:

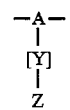

in which

A is a crosslinked carbon chain;

Y is an optional spacer group; and

Z is an ionic or polar functional group.

41. The functionalized microbeads of claim 40 wherein the ratio of 10% sodium chloride absorption by the functionalized microbeads to water absorption is greater than about 0.1.

42. The functionalized microbeads of claim 41 wherein the ratio of 10% sodium chloride absorption to water absorption is greater than about 0.5.

43. The functionalized microbeads of claim 42 wherein the ratio of 10% sodium chloride absorption to water absorption is greater than about 0.7.

44. The functionalized microbeads of claim 40 wherein Z is selected from the group consisting of an alkyl cationic quaternary ammonium group having 10 carbon atoms or less;

an alkyl amine salt group having 8 carbon atoms or less;

an alkoxylate group;

a metal, ammonium, or substituted ammonium salt of a sulfuric, carboxylic, phosphoric or sulfonic acid group, except that where Z is a sulfonic acid; Y does not have the structure:

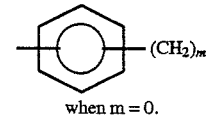

when m = 0.

45. The functionalized microbeads of claim 40 wherein Z comprises an ionic or polar functional group selected from the group consisting of structures 1–2:

in which $R_2$, $R_3$, and $R_4$ can be the same or different and are selected from the group consisting of an alkyl, cycloalkyl, aryl, and hydroxyalkyl; or $R_2$ and $R_3$ form part of a ring system; and the number of carbons present in $R_2+R_3+R_4$ is less than 10 for a cationic quaternary ammonium (1);

the number of carbons present in $R_2+R_3$ is less than 8 for an amine salt (2); and the counterion $X^-$ is an inorganic ion or a carboxylate group having less than 8 carbons.

46. The functionalized microbeads of claim 40 wherein Z is an alkoxylate group having the structure:

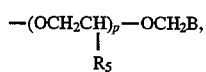

where p is 1 to 680, and

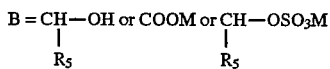

and where $R_5$ is a hydrogen or an alkyl group, and M is a metal, an ammonium, or a substituted ammonium cation.

47. The functionalized microbeads of claim 40 wherein the level of crosslinking is from about 1 to about 20%.

48. The functionalized microbeads of claim 40 wherein the level of crosslinking is from about 2 to about 10%.

49. The functionalized microbeads of claim 40 wherein the void volume of the microbeads is greater than about 80%.

50. The functionalized microbeads of claim 40 wherein the degree of functionalization is greater than about 50%.

51. The microbeads of claim 3 wherein the microbeads have a carboniferous structure.

52. The carboniferous microbeads of claim 51 wherein the microbeads have a void volume of at least about 80%.

53. The microbeads of claim 3 additionally comprising a gel or pre-gel within the cavities of the microbeads, wherein the gel or pre-gel comprises a chemical group that interacts with a chemical entity selected from the group consisting of a component of a solution and a reactant in a chemical synthesis.

54. The microbeads of claim 53 wherein the cavity size is in the range of about 1 to about 50 µm in diameter.

55. The microbeads of claim 53 wherein the microbeads are crosslinked such that, in the presence of liquid, microbead swelling does not exceed approximately two times the microbead dry volume.

56. The microbeads of claim 53 wherein the ratio by weight of swollen gel to microbeads lies in the range of about 60:40 to about 95:5.

57. A process for producing the microbeads of claim 53 comprising
 a. producing porous, crosslinked polymeric microbeads having cavities joined by interconnecting pores and
 b. depositing and retaining a gel or pre-gel in the microbead cavities.

58. The process of claim 57 wherein step (b) comprises contacting the microbeads with a solution comprising pre-gel components and a swelling solvent for the microbeads for a time sufficient to allow the pre-gel components to permeate the swollen microbeads and form a gel within the microbead cavities.

59. The microbeads of claim 3 wherein a molecule selected from the group consisting of a polypeptide and an oligonucleotide is attached to the surface of the microbeads.

60. The microbeads of claim 59 wherein the molecule is a polypeptide selected from the group consisting of an antibody, a lectin, an enzyme, and a hapten.

61. The microbeads of claim 59 wherein the molecule is attached to the surface of the microbeads by a type of attachment selected from the group consisting of non-covalent adsorption, covalent bonding, and attachment via a bridging molecule.

62. The process of claim 23, wherein the polymeric stabilizer comprises ethyl cellulose.

63. The process of claim 4 wherein the stabilizer is present in the oil phase at a concentration in the range of about 0.01 to about 1 weight percent.

64. The process of claim 63 wherein the stabilizer is present in the oil phase at a concentration in the range of about 0.02 to about 0.6 weight percent.

65. The process of claim 21 wherein the emulsion additionally comprises an inert solvent that is capable of solubilizing the stabilizer and is miscible in the oil phase of the HIPE.

66. The process of claim 65 wherein the inert solvent is a halogenated solvent.

67. The process of claim 65 wherein the inert solvent is selected from the group consisting of trichloroethane, toluene, and chloroform.

68. The process of claim 65 wherein the inert solvent is present in the oil phase at a concentration in the range of about 3 to about 60 weight percent.

69. The process of claim 68 wherein the inert solvent is present in the oil phase at a concentration in the range of about 10 to about 40 weight percent.

70. The process of claim 14 wherein the suspending agent comprises acacia gum.

71. The process of claim 15 wherein the suspending agent is present in the aqueous suspension medium at a concentration of about 2 to about 15 weight percent.

* * * * *